(12) United States Patent
Smith

(10) Patent No.: US 9,022,928 B2
(45) Date of Patent: May 5, 2015

(54) WOUND PROTECTOR INCLUDING BALLOON WITHIN INCISION

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 51 days.

(21) Appl. No.: 13/415,993

(22) Filed: Mar. 9, 2012

(65) Prior Publication Data

US 2012/0238825 A1 Sep. 20, 2012

Related U.S. Application Data

(60) Provisional application No. 61/454,113, filed on Mar. 18, 2011.

(51) Int. Cl.
*A61B 1/32* (2006.01)
*A61B 17/34* (2006.01)
*A61B 17/00* (2006.01)

(52) U.S. Cl.
CPC ..... *A61B 17/3423* (2013.01); *A61B 2017/3419* (2013.01); *A61B 2017/00557* (2013.01)

(58) Field of Classification Search
CPC ........... A61B 2017/00535; A61B 2017/00557; A61B 17/3423; A61B 2017/3435
USPC ................................................. 600/201–246
See application file for complete search history.

(56) References Cited

U.S. PATENT DOCUMENTS

| 5,366,478 | A | 11/1994 | Brinkerhoff et al. |
| 5,556,385 | A | 9/1996 | Andersen |
| 5,735,791 | A * | 4/1998 | Alexander et al. ............... 600/37 |
| 6,033,426 | A | 3/2000 | Kaji |
| 6,048,309 | A | 4/2000 | Flom et al. |
| 6,059,816 | A | 5/2000 | Moenning |
| 6,328,720 | B1 | 12/2001 | McNally et al. |
| 6,623,426 | B2 | 9/2003 | Bonadio et al. |
| 6,916,331 | B2 | 7/2005 | Mollenauer et al. |
| 6,972,026 | B1 | 12/2005 | Caldwell et al. |
| 7,052,454 | B2 | 5/2006 | Taylor |

(Continued)

FOREIGN PATENT DOCUMENTS

| EP | 1 312 318 A1 | 5/2003 |
| EP | 2 005 907 A2 | 12/2008 |

(Continued)

OTHER PUBLICATIONS

Extended European Search Report dated Apr. 19, 2012 in European Application No. EP 12152164; 7 pgs.

(Continued)

*Primary Examiner* — Ellen C Hammond
*Assistant Examiner* — Christina Negrellirodrigue

(57) ABSTRACT

A surgical access device is disclosed herein. The surgical access device includes a housing adapted for insertion into an incision in tissue and at least one inflatable portion disposed on the housing. The housing defines a proximal end and a distal end and has a lumen extending therethrough for the reception of a surgical access portal. The at least one inflatable portion has a deflated state and an inflated state and the housing is insertable into the incision in tissue when the at least one inflatable portion is in the deflated state. The housing is adapted to form a substantially fluid tight seal with the incision in tissue and with a surgical access portal inserted therethrough when the at least one inflatable portion is in the inflated state.

18 Claims, 11 Drawing Sheets

(56) References Cited

U.S. PATENT DOCUMENTS

| | | |
|---|---|---|
| 7,100,614 B2 | 9/2006 | Stevens et al. |
| 7,850,600 B1 | 12/2010 | Piskun |
| 2005/0288558 A1 | 12/2005 | Ewers et al. |
| 2006/0149306 A1 | 7/2006 | Hart et al. |
| 2006/0161049 A1 | 7/2006 | Beane et al. |
| 2007/0225650 A1 | 9/2007 | Hart et al. |
| 2008/0027476 A1 | 1/2008 | Piskun |
| 2008/0200767 A1* | 8/2008 | Ewers et al. ............ 600/208 |
| 2009/0221966 A1 | 9/2009 | Richard |
| 2010/0249524 A1* | 9/2010 | Ransden et al. .......... 600/207 |
| 2010/0312066 A1 | 12/2010 | Cropper et al. |

FOREIGN PATENT DOCUMENTS

| | | |
|---|---|---|
| EP | 2 044 889 A1 | 4/2009 |
| EP | 2 098 182 A2 | 9/2009 |
| EP | 2 238 925 A1 | 10/2010 |
| EP | 2 289 438 A1 | 3/2011 |
| EP | 2 343 019 A1 | 7/2011 |
| WO | WO 96/36283 | 11/1996 |
| WO | WO 00/54675 A1 | 9/2000 |
| WO | WO 01/08581 A2 | 2/2001 |
| WO | WO 03/034908 A2 | 5/2003 |
| WO | WO 2004/030515 A2 | 4/2004 |
| WO | WO 2004/075741 A2 | 9/2004 |
| WO | WO 2009/048542 A2 | 4/2009 |

OTHER PUBLICATIONS

Extended European Search Report dated Apr. 20, 2012 in European Application No. EP 12152128; 7 pgs.

Extended European Search Report dated Jun. 5, 2012 in European Application No. EP 11250793.4; 10 pgs.

Extended European Search Report from Application No. EP 12159854.4 dated Aug. 8, 2014.

* cited by examiner

WOUND PROTECTOR INCLUDING BALLOON WITHIN INCISION

CROSS REFERENCE TO RELATED APPLICATION

The present application claims the benefit of and priority to U.S. Provisional Application Ser. No. 61/454,113, filed on Mar. 18, 2011, the entire contents of which are incorporated herein by reference.

BACKGROUND

1. Technical Field

The present disclosure relates generally to surgical instruments for use with a seal anchor member. More particularly, the present disclosure relates to an incision or orifice protection device usable with a seal anchor member that provides additional protection for incisions or other natural orifices during minimally invasive surgical procedures and allows for the use of standard sized surgical access portals through incisions of varying size.

2. Description of Related Art

Increasingly, many surgical procedures are performed through small incisions in the skin. As compared to the larger incisions typically required in traditional procedures, smaller incisions result in less trauma to the patient. By reducing the trauma to the patient, the time required for recovery is also reduced. Generally, the surgical procedures that are performed through small incisions in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single incision or a naturally occurring orifice (i.e. mouth, anus, or vagina) while allowing multiple instruments to be inserted through the device to access the working space beyond the device.

However, a continuing need exists for a protection system which minimizes damage to the single incision or naturally occurring orifice during a surgical procedure and which also allows for the use of standard sized surgical access devices through incisions or orifices of varying size.

SUMMARY

A surgical access device is disclosed herein. The surgical access device includes a housing adapted for insertion into an incision in tissue and at least one inflatable portion disposed on the housing. The housing defines a proximal end and a distal end and has a lumen extending therethrough for the reception of a surgical access portal. The at least one inflatable portion has a deflated state and an inflated state and the housing is insertable into the incision in tissue when the at least one inflatable portion is in the deflated state. The housing is adapted to form a substantially fluid tight seal with the incision in tissue and with a surgical access portal inserted therethrough when the at least one inflatable portion is in the inflated state. The at least one inflatable portion may also include a partially inflated state. The at least one inflatable portion may fully surround the housing, may be disposed on an exterior surface of the housing, an interior surface of the housing or both. The at least one inflatable portion may include three inflatable portions.

The at least one inflatable portion may be slidable proximally and distally along the exterior surface of the housing and the housing may further include a slide member attached to the exterior surface of the housing where the at least one inflatable portion is slidably mounted on the slide member. The slide member may further include a guide ring disposed at a proximal end where the guide ring is adapted to guide a tube toward the at least one inflatable portion and the tube may be adapted to actuate the at least one inflatable portion proximally and distally along the slide member.

The at least one inflatable portion may include a tube extending proximally therefrom which is adapted to provide fluid to the at least one inflatable portion from a fluid source connected to the tube. The tube may be disposed within the housing or may be disposed on the housing.

The housing may also include a crescent shaped ring disposed at the proximal end where at least a portion of the housing is wrapped around the ring such that the ring is rotatable to increase or decrease the length of the housing.

A surgical access system for large incisions is also disclosed and includes a surgical access portal having at least one lumen which is adapted for sealed reception of a surgical object therethrough and a surgical access device as disclosed above. The surgical access device includes a housing which is adapted for insertion into an incision in tissue and at least one inflatable portion disposed on the housing. The housing defines a proximal end and a distal end and has a lumen extending therethrough for the reception of the surgical access portal.

The at least one inflatable portion has a deflated state and an inflated state and the housing is insertable into the incision in tissue when the at least one inflatable portion is in the deflated state. The housing forms a substantially fluid tight seal with the incision in tissue and with a surgical access portal inserted therethrough when the at least one inflatable portion is in the inflated state.

A method of providing surgical access through a large incision in tissue is also disclosed. The method includes providing a surgical access portal and a surgical access device as described above. The surgical access portal includes at least one lumen adapted for the sealed reception of a surgical object therethrough. The surgical access device includes a housing which is adapted for insertion into an incision in tissue and at least one inflatable portion disposed on the housing. The housing defines a proximal end and a distal end and has a lumen extending therethrough for the reception of the surgical access portal. The at least one inflatable portion has a deflated state and an inflated state and the housing is insertable into the incision in tissue when the at least one inflatable portion is in the deflated state. The housing forms a substantially fluid tight seal with the incision in tissue and with a surgical access portal inserted therethrough when the at least one inflatable portion is in the inflated state.

The method also includes inserting the housing into the incision in tissue, at least partially inflating the at least one inflatable portion to secure the housing within the incision in tissue, inserting the surgical access portal through the lumen of the housing and further inflating the at least one inflatable portion to secure the surgical access portal within the lumen.

The at least one inflatable portion may be slideable proximally and distally along an exterior surface of the housing and the method may include the step of sliding the at least one inflatable portion proximally or distally along the exterior surface of the housing.

The surgical access device may include a tube extending proximally from the housing and being in fluid communication with the at least one inflatable member and the method may include the step of attaching a fluid source to the tube and dispensing fluid to the at least one inflatable portion.

BRIEF DESCRIPTION OF THE DRAWINGS

The accompanying drawings, which are incorporated in and constitute a part of this specification, illustrate embodiments of the presently disclosed surgical access device, and together with a general description of the disclosed surgical access device given above, and the detailed description of the embodiments given below, serve to explain the principles of the disclosed surgical access device.

FIG. 7A is a detailed view of the proximal arm of the surgical access device of FIG. 7.

DETAILED DESCRIPTION

Figure 1:
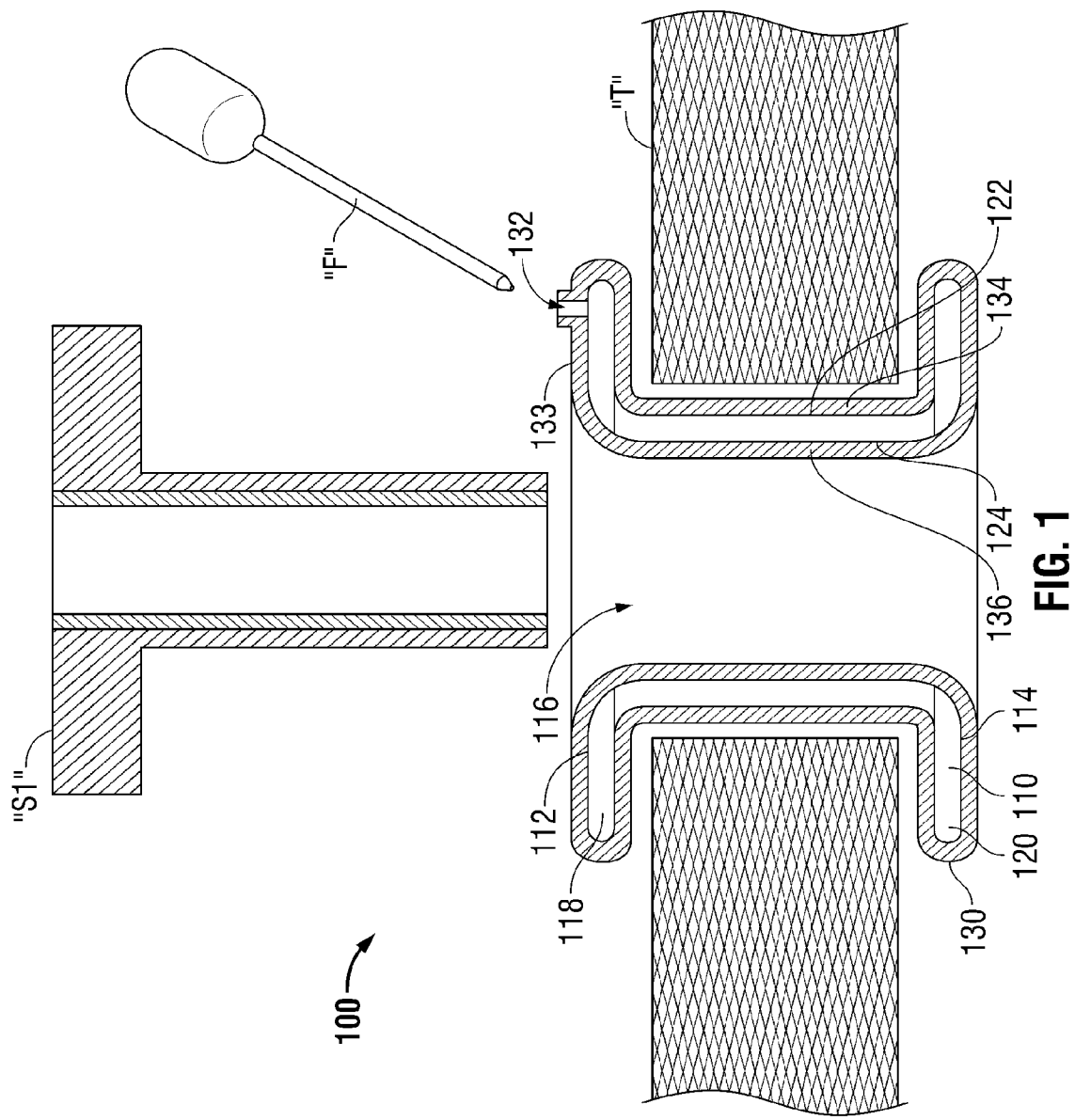
FIG. 1 is a side cut-away view of a surgical access device in accordance with the present disclosure.

Disclosed herein is a surgical access device for protecting an incision in tissue or natural orifice during minimally invasive surgery. More specifically a surgical access device is disclosed which is insertable into a single incision or natural orifice in a body and capable of providing a protective layer between the incision or natural orifice and surgical objects or surgical access portals inserted therethrough. The surgical access device also allows standard sized surgical access portals to be used through incisions or natural orifices of varying sizes and specifically allows a surgical access portal to be used through an incision or natural orifice that is larger than the surgical access portal.

Particular embodiments of the presently disclosed surgical access device are described in detail with reference to the drawing figures wherein like reference numerals identify similar or identical elements. As used herein, the term "distal" refers to that portion which is farther from the user while the term "proximal" refers to that portion which is closer to the user or surgeon. While the term "incision" is used to describe an opening in tissue through which the disclosed surgical access device is inserted it is contemplated that the opening may alternatively be any natural orifice such as, for example, the anus or vagina.

Figure 2:
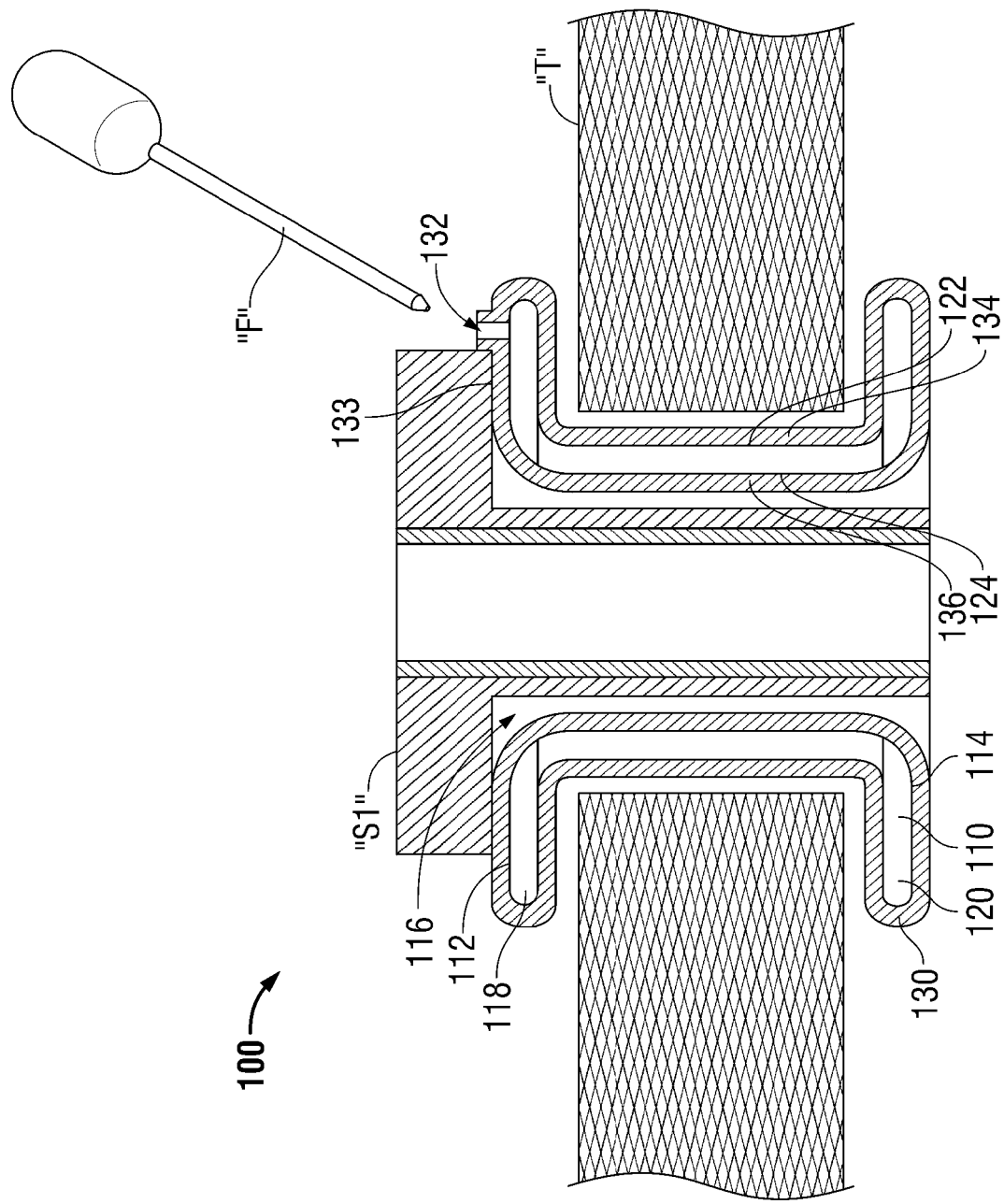
FIG. 2 is a side cut-away view of the surgical access device of FIG. 1 after insertion of a surgical access portal therethrough.
Figure 3:
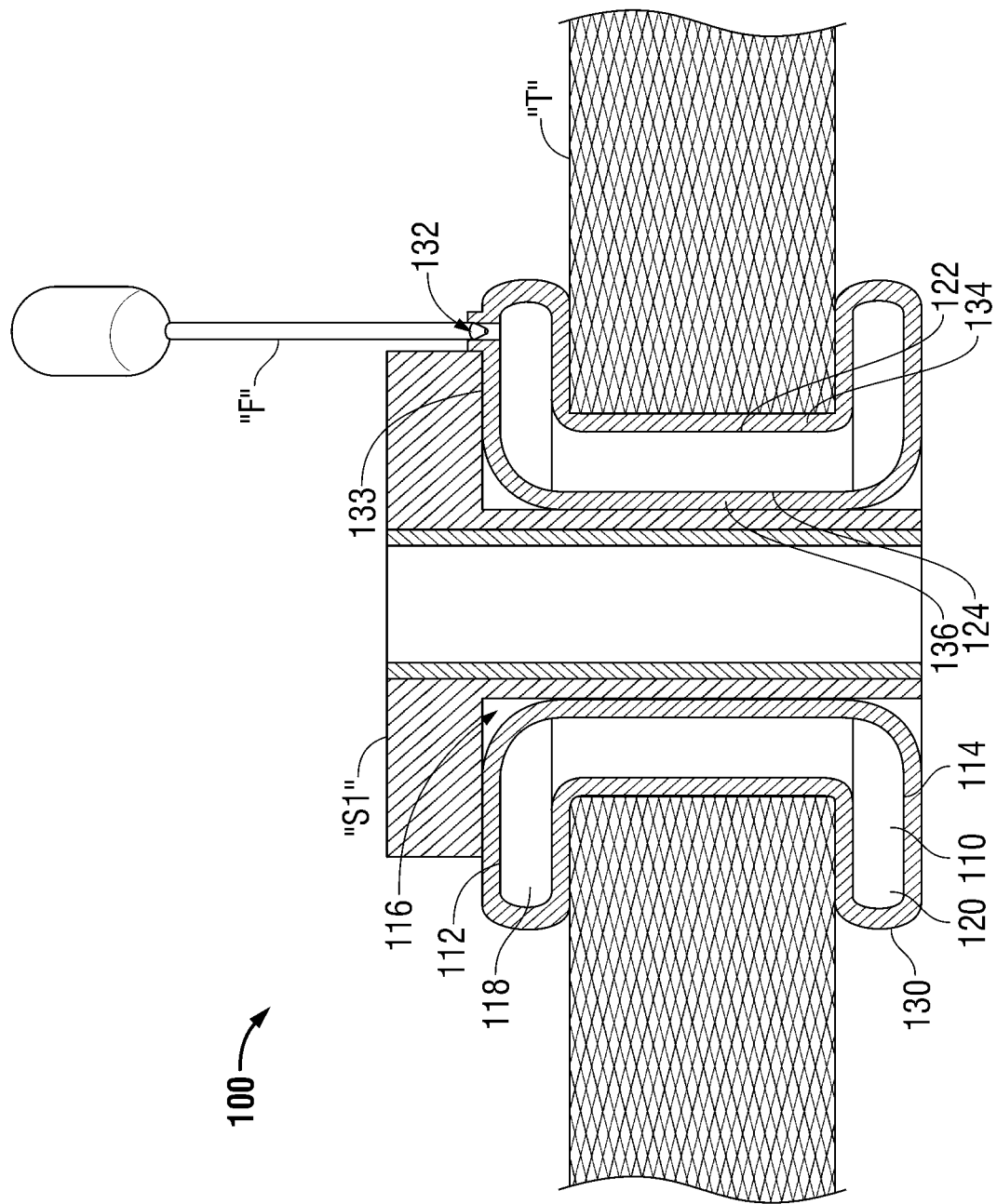
FIG. 3 is a side cut-away view of the surgical access device of FIG. 2 after inflation of the inflatable portion.

Referring now to FIGS. 1-3, a surgical access device 100 is disclosed including a housing 110 and an inflatable portion 130 disposed on housing 110. Housing 110 is insertable into an incision in tissue "T" and defines a proximal end 112, a distal end 114 and a lumen 116 therethrough for the reception of a surgical access portal "S1" therethrough in a substantially fluid-tight manner. It is contemplated that surgical access portals of various shapes and sizes may be inserted through lumen 116 including a surgical access portal "S1", as seen in FIGS. 1-3, having a single proximal flange, a surgical access portal "S2", as seen in FIGS. 4 and 6-9, having both proximal and distal flanges or any other surgical access portals as known in the art. Each surgical access portal "S1", "S2" further includes one or more lumen extending therethrough for the fluid-tight reception of surgical objects or surgical instruments. Throughout the present disclosure it is contemplated that surgical access portals "S1" and "S2" are fully interchangeable. A suitable access portal is disclosed in U.S. patent application Ser. No. 12/244,024 which is now incorporated by reference herein. It is contemplated that lumen 116 may also receive other surgical objects as known in the art. Housing 110 defines a "U" shaped cross-section and includes flanged portions 118 and 120 at proximal and distal ends 112 and 114 respectively to provide a shape for inflatable portion 130 and to assist in positioning housing 110 properly in the incision in tissue "T". Inflatable portion 130 is disposed on housing 110 and may fully surround housing 110. Inflatable portion 130 includes an opening 132 disposed at a proximal end 133 and may include one or more valves (not shown) disposed within or near opening 132 for maintaining a fluid-tight seal therein. Opening 132 is adapted to receive a syringe or other fluid source "F" or may be connected to any other fluid providing system as known in the art.

Inflatable portion 130 is inflatable to secure housing 110 within incision in tissue "T" and for securing surgical access portal "S1" within housing 110 in a substantially fluid-tight manner. It is contemplated that inflatable portion 130 may include two or more independently inflatable sections 134 and 136 where section 134 is disposed on an outer surface 122 of housing 110 and section 136 is disposed on an inner surface 124 of housing 110.

Surgical access device 100 has a deflated state, where inflatable portion 130 is deflated and housing 110 is insertable into an incision in tissue "T", and an inflated state, where inflatable portion 130 is sufficiently inflated to secure housing 110 within incision in tissue "T". The amount of inflation required for the inflated state is based on the size of the incision and the size of the surgical access portal to be inserted through the housing. It is contemplated that inflatable portion 130 may also have a partially inflated state to assist in securing housing 110 within incision in tissue "T" and that, upon insertion of surgical access portal "S1" through lumen 116 of housing 110, inflatable portion 130 may be further inflated to the inflated state to provide lumen 116 with a reduced diameter for securing surgical access portal "S1" in place. If independently inflatable sections 134 and 136 are provided it is contemplated that section 134 may be inflated to secure housing 110 in incision in tissue "T" and that section 136 may be separately inflated to secure surgical access portal "S1" in place.

During use, housing 110 is inserted into an orifice or incision in tissue "T" while inflatable portion 130 is in the deflated state. After insertion a physician or surgeon inserts or attaches a fluid source "F" to opening 132 to provide fluid to inflatable portion 130. The surgeon at least partially fills inflatable portion 130 to achieve the partially inflated state thereby securing housing 110 in place. Once housing 110 is secure a surgical access portal "S1" is inserted through lumen 116. The surgeon then provides additional fluid to inflatable portion 130 to achieve the inflated state, providing lumen 116 with a reduced diameter for securing surgical access portal "S1" in place in a substantially fluid-tight manner. In this way a surgical access portal of standard size may be utilized through an incision in tissue or naturally occurring orifice which has a larger diameter than the surgical access portal. It is contemplated that surgical access portal "S1" may be inserted into housing 110 prior to any inflation of inflatable portion 130. It is also contemplated that inflatable portion 130 may be partially deflated during the operation to allow surgical access portal "S1" to be inserted and/or removed. This allows the surgeon to use other surgical objects or instruments through housing 110 which may be too large for surgical access portal "S1". Also, the deflation or partial deflation of the inflatable portion 130 enables a specimen to be removed and/or passed through the incision (e.g., the permanent removal of diseased internal anatomy and/or the temporary exteriorization of portions of the colon to be manipulated outside of the body before being returned to inside the body) without the need to remove the entire housing 110, thereby providing, via the housing 110, a protective layer for the incision against, e.g., contamination via cancer cell seeding or the like. Still further, because of the ability of a user to deflate or partially deflate the inflatable portion 130, the user may selectively increase the size of the incision during the course of the surgical procedure (e.g., a surgeon may make an initial relatively small incision—such that the surgical access portal is maintained in the incision without the inflatable portion 130 being inflated—and may later, if the surgeon decides that doing so is warranted, make a larger incision—such that the surgical access portal is maintained in the incision with the inflatable portion 130 being fully or partially inflated. This flexibility may enable a surgeon to minimize the size of the incision made during the surgical procedure, as the surgeon may wait to make a larger incision until after he or she has determined, using the initially smaller incision, to enlarge the incision based on his or her observations. It also enables the surgeon to utilize the same surgical access portal regardless of the size of the incision and regardless of whether the surgeon elects to make an initially small incision or to make an initially larger incision, thereby eliminating the need for different sized surgical access portals. It should be noted that these above-described benefits are applicable to all of the embodiments set forth herein. After the operation the surgeon deflates inflatable portion 130 to remove surgical access portal "S1" from lumen 116 of housing 110 and to remove housing 110 from the incision in tissue "T".

Figure 4:
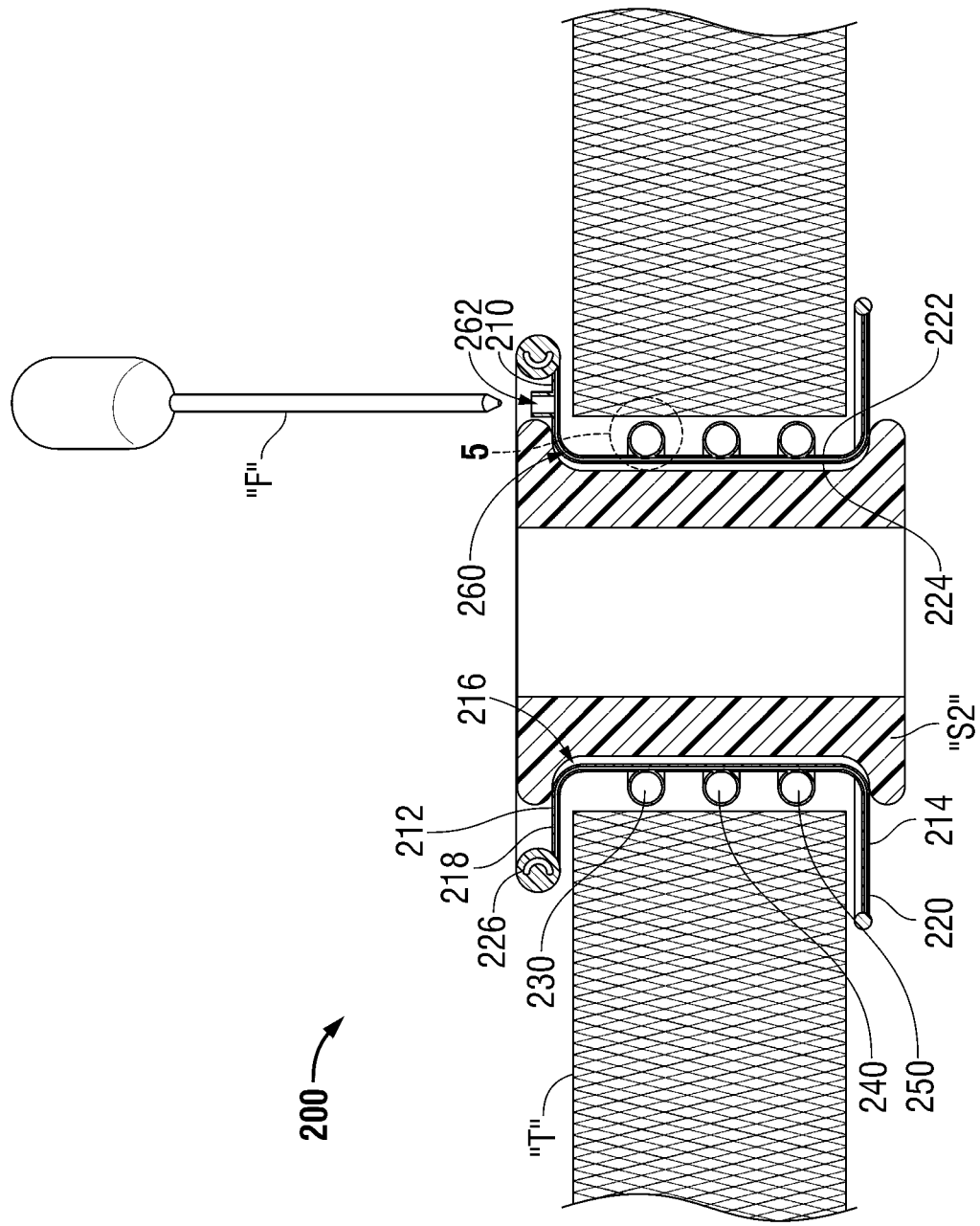
FIG. 4 is a side cut-away view of an alternate embodiment of the surgical access device of FIG. 1 having multiple inflatable portions.
Figure 5:
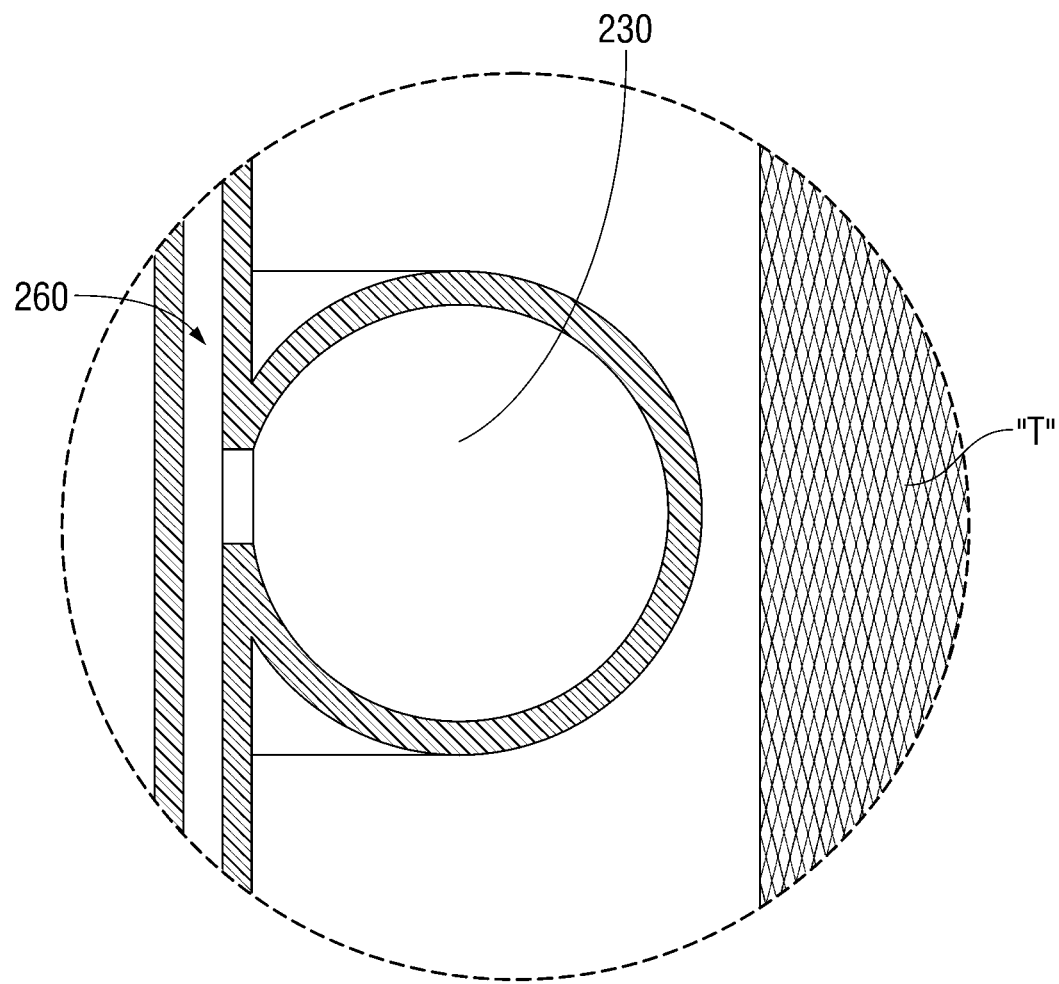
FIG. 5 is a detailed view of one of the inflatable portions of surgical access device of FIG. 4.
Figure 6:
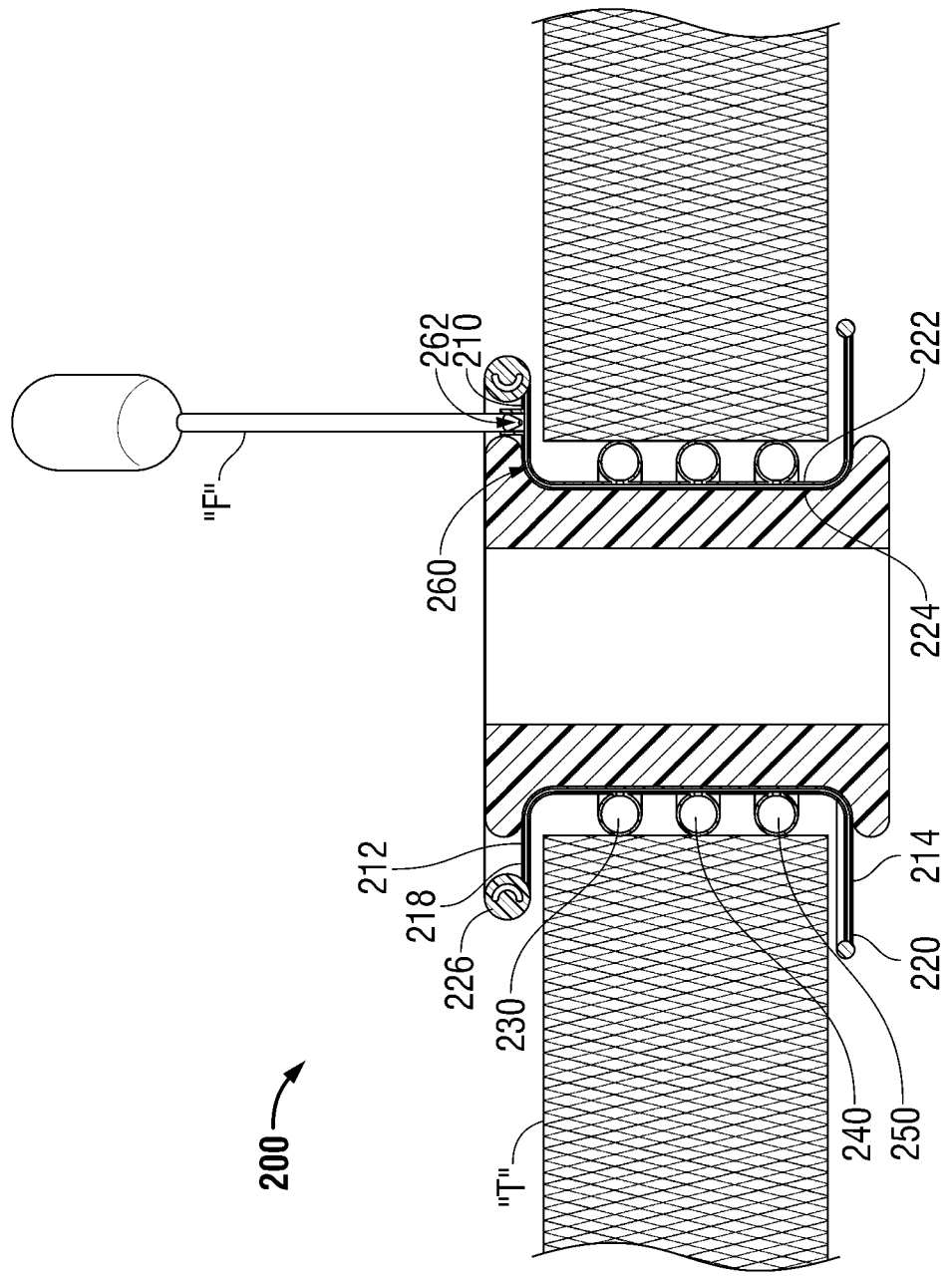
FIG. 6 is a side cut-away view of the surgical access device of FIG. 4 after inflation of the inflatable portion.

Referring now to FIGS. 4-6, in another embodiment which is similar to the previous embodiment, surgical access device 200 includes a housing 210 and at least one inflatable portion 230 disposed on housing 210. It is contemplated that housing 210 may include three inflatable portions 230, 240 and 250. Housing 210 is insertable into an orifice or incision in tissue "T" and defines a "U" shaped cross-section including flanged portions 218 and 220 at proximal and distal ends 212 and 214 respectively. It is further contemplated that proximal end 212 may include an arcuate or crescent shaped ring 226 around which at least a portion of housing 210 is wrapped such that rotation of ring 226 allows the length of housing 210 to be extended or reduced at proximal end 212. Housing 210 also includes a lumen 216 extending therethrough for the reception of a surgical access port "S2" in a substantially fluid-tight manner. It is contemplated that lumen 216 may also receive other kinds of surgical objects, as known in the art.

In this embodiment inflatable portions 230, 240 and 250 are disposed on an exterior surface 222 of housing 210 although it is contemplated that inflatable portions 230, 240 and 250 may be disposed on an interior surface 224 or on both exterior surface 222 and interior surface 224. Inflatable portions 230, 240 and 250 may be spaced apart from one another or may be proximate to or abutting one another. It is also contemplated that inflatable portions 230, 240 and 250 may be initially spaced apart when in the deflated state and abutting or proximate to one another when in the inflated state. Each inflatable portion 230, 240 and 250 may be independently inflatable or inflatable portions 230, 240 and 250 may be concurrently inflatable.

Housing 210 may also include one or more inflation lumens 260 in fluid communication with inflatable portions 230, 240 and 250 and defining an opening 262 for the reception of a fluid source "F". Inflation lumens 260 may be disposed within housing 210 or alternatively may be disposed on exterior surface 222 or interior surface 224 of housing 210. It is also contemplated that each inflatable portion 230, 240 and 250 may have a separate inflation lumen 260 and that each inflation lumen 260 may have a separate opening 262.

During use, inflatable portions 230, 240 and 250 are initially in the deflated state. The surgeon inserts housing 210 into an incision in tissue "T" and adjusts the length of housing 210 by rotating ring 226 clockwise or counter-clockwise depending on the depth of the incision in tissue "T". Once housing 210 is positioned within the incision in tissue "T" a fluid source "F" is inserted into or attached to opening 262 and fluid is provided to inflatable portions 230, 240 and 250 to transition them to the inflated state. As inflatable portions 230, 240 and 250 expand they come into contact with the incision in tissue "T" and thereby secure housing 210 in place in a substantially fluid-tight manner. It is contemplated that inflatable portions 230, 240 and 250 may be only partially inflated. A surgeon may then insert a surgical access portal "S2" into lumen 216 of housing 210 and further fill inflatable portions 230, 240 and 250 with fluid reduce the diameter of lumen 216 and thereby cause housing 210 to press against surgical access portal "S2". This secures surgical access portal "S2" in place and creates a substantially fluid-tight seal between housing 210 and surgical access portal "S2". In this way a surgical access portal of standard size may be utilized through an incision in tissue or naturally occurring orifice which has a larger diameter than the surgical access portal. It is also contemplated that only one of inflatable portions 230, 240 or 250, or any combination thereof may be inflated or partially inflated such that a surgical access portal "S2" inserted through lumen 216 may be allowed some freedom of movement during the surgery while still maintaining a fluid-tight seal therewith. To remove surgical access portal "S2" the surgeon may evacuate fluid from inflatable portions 230, 240 and 250 to achieve the partially inflated or deflated states.

Figure 7:
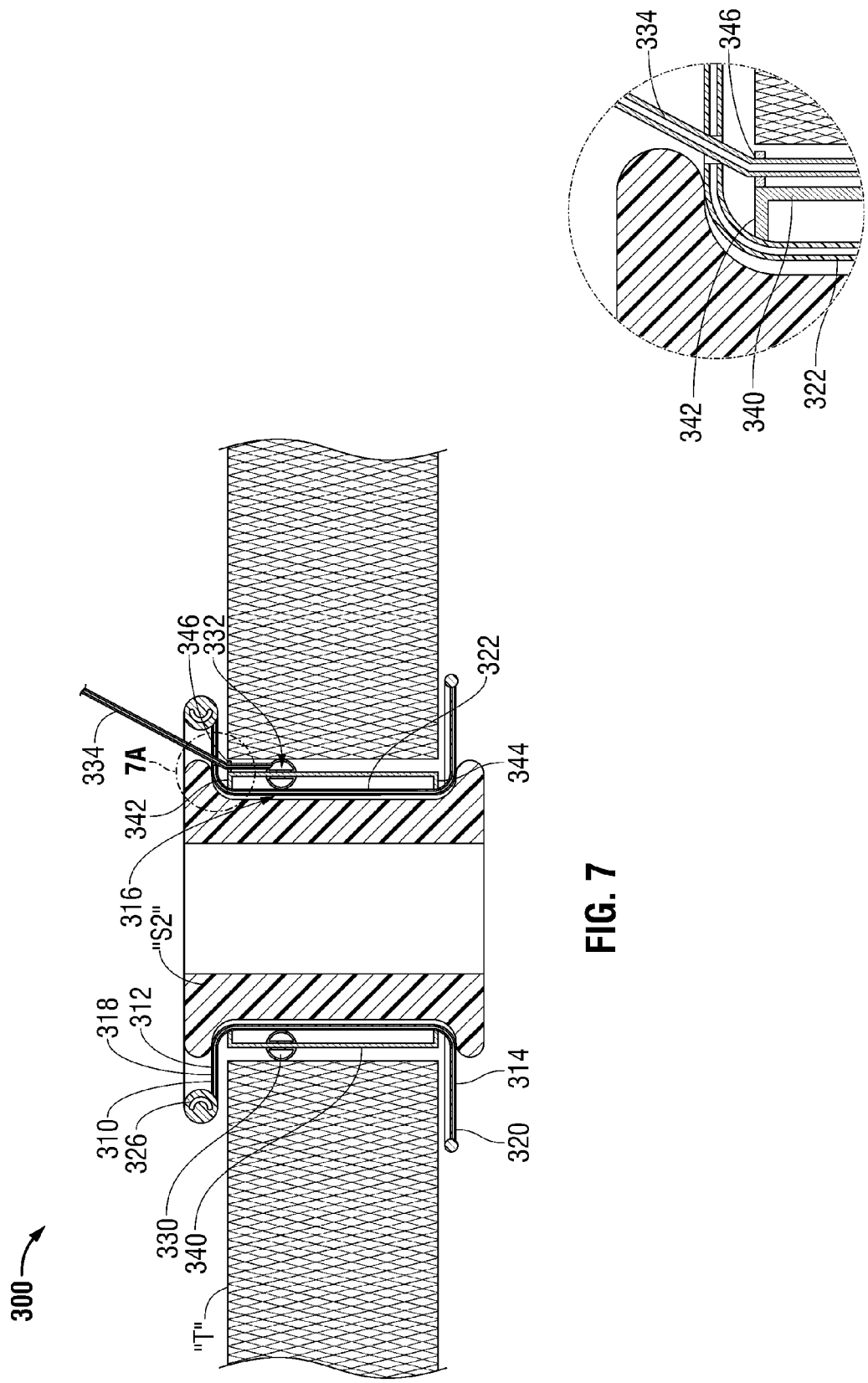
FIG. 7 is a side cut-away view of an alternate embodiment the surgical access device of FIG. 1 with a slideable inflatable portion.
Figure 8:
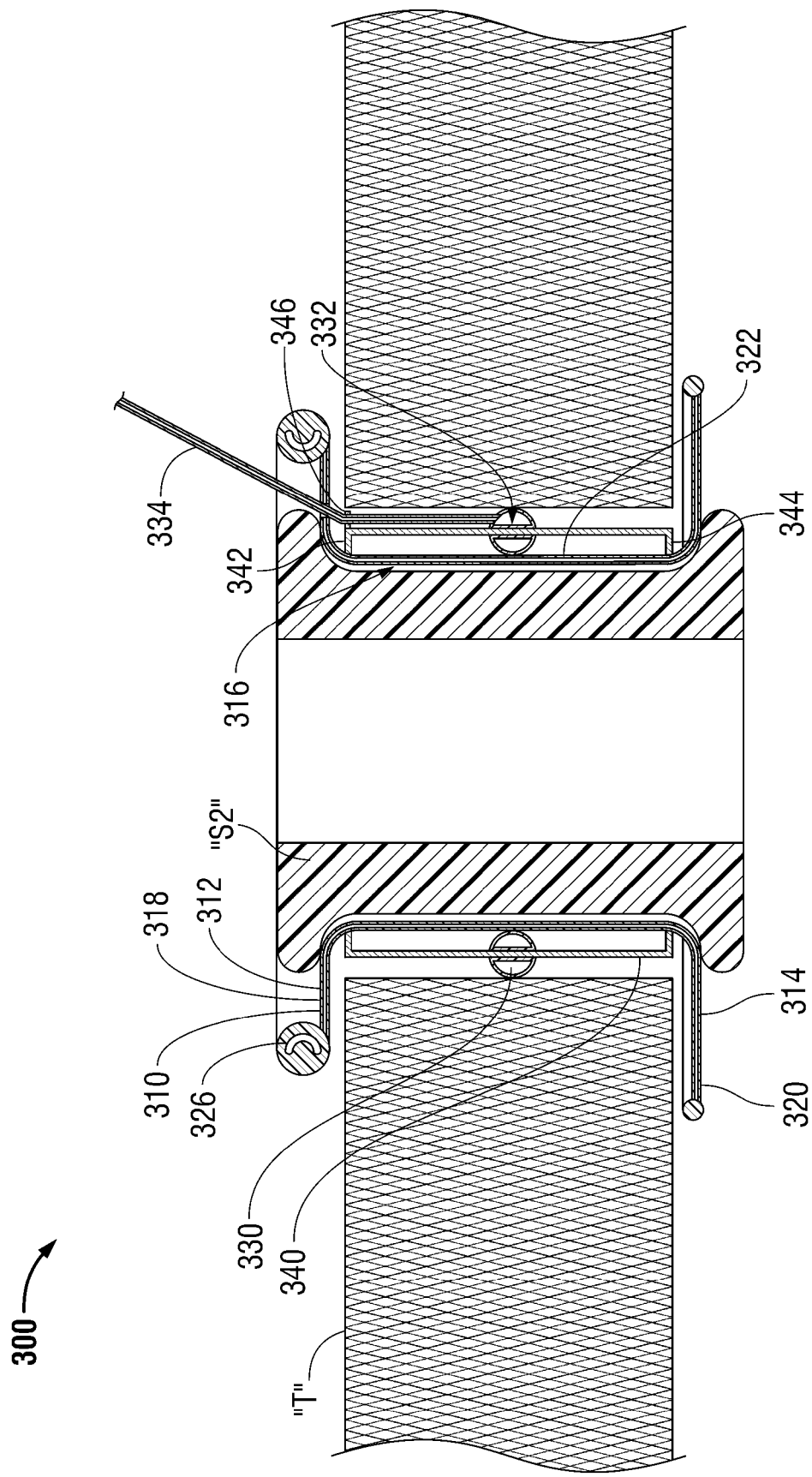
FIG. 8 is a side cut-away view of the surgical access device of FIG. 7 with the inflatable portion positioned halfway along the slide member.
Figure 9:
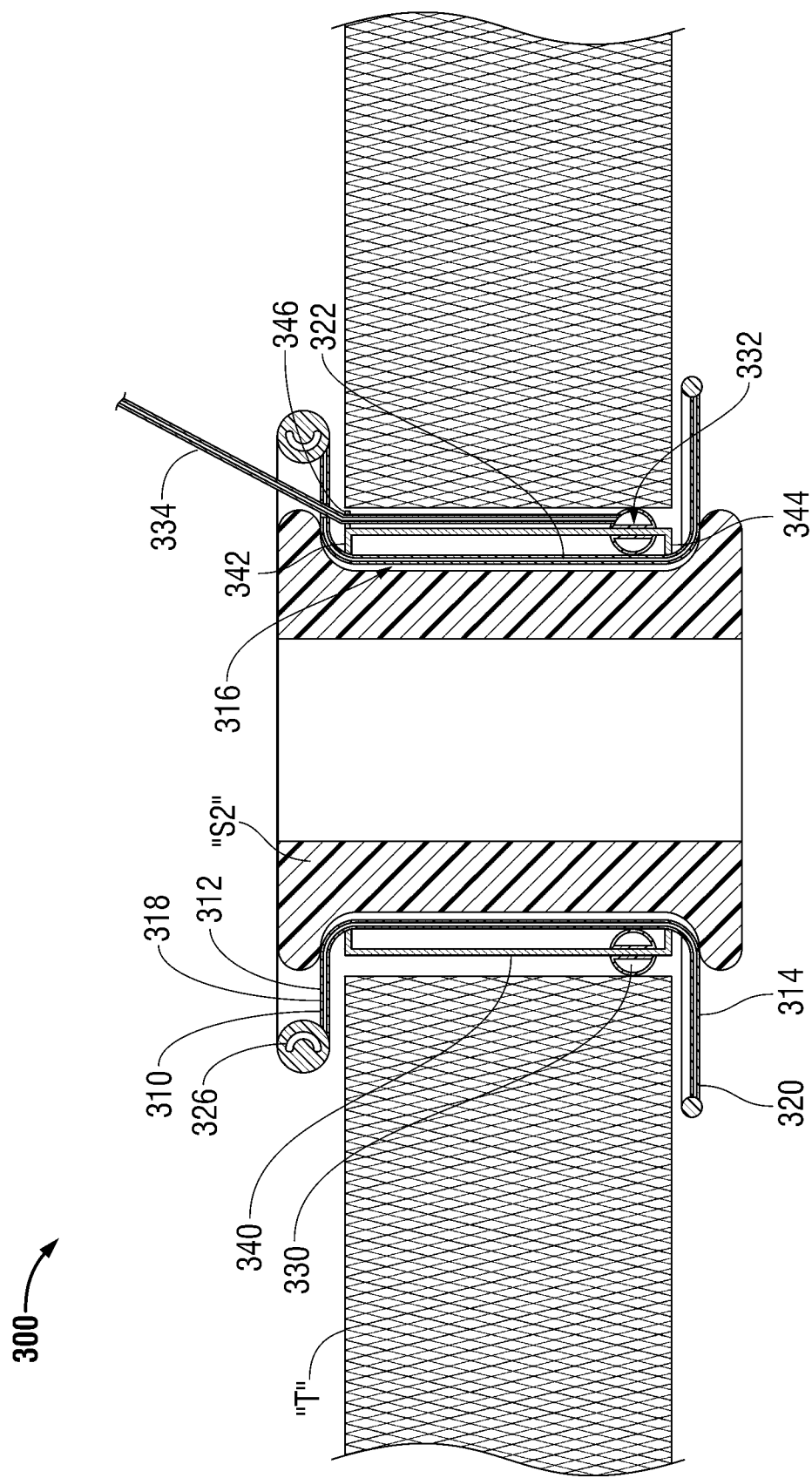
FIG. 9 is a side cut-away view of the surgical access device of FIG. 7 with the inflatable portion positioned at the distal end of the slide member.

Referring now to FIGS. 7-9, in another embodiment, similar to previous embodiments, surgical access device 300 includes a housing 310, a slide member 340 attached to housing 310 and an inflatable portion 330 slidably mounted to slide member 340. Housing 310 is insertable into an orifice or incision in tissue "T" and defines a "U" shaped cross-section including flanged portions 318 and 320 at proximal and distal ends 312 and 314 respectively. It is further contemplated that proximal end 312 may include an arcuate or crescent shaped ring 326 around which at least a portion of housing 310 is wrapped such that rotation of ring 326 allows the length of housing 310 to be extended or reduced at proximal end 312. Housing 310 also includes a lumen 316 extending therethrough for the reception of a surgical access port "S2" in a substantially fluid-tight manner. It is contemplated that lumen 316 may also receive other surgical objects as known in the art.

Slide member 340 is spaced apart from housing 310 and is attached to an exterior surface 322 of housing 310 by a proximal arm 342 and a distal arm 344. Inflatable portion 330 includes a lumen 332 extending therethrough for the reception of slide member 340 and is slideable along slide member 340 between proximal arm 342 and distal arm 344. A tube 334 is connected to inflatable portion 330 and may be inserted through a mounting member, e.g., ring or bracket, 346 extending from or through proximal arm 342 of slide member 340 to help guide tube 334 to inflatable portion 330, as can be seen in further detail in FIG. 7A. Tube 334 may be used to move inflatable portion 330 proximally and distally between proximal arm 342 and distal arm 344 in addition to providing fluid communication to inflatable portion 330 for inflation and deflation. As with previous embodiments, inflatable portion 330 has a deflated state and an inflated state and may also be only partially inflated.

During use, the surgeon inserts housing 310 into an incision in tissue "T" with inflatable portion 330 in the deflated state and disposed between exterior surface 322 and the incision in tissue "T". The surgeon may adjust the length of housing 310 by rotating ring 326 clockwise or counter-clockwise depending on the depth of the incision in tissue "T" and may adjust the position of inflatable portion 330 by sliding tube 334 proximally or distally through mounting ring 346 to move inflatable portion 330 proximally or distally along slide member 340. Once inflatable portion 330 is in the desired position the surgeon may provide fluid to inflatable portion 330 through tube 334 to transition inflatable portion 330 from the deflated state to the inflated state to secure housing 310 within the incision in tissue "T". It is contemplated that the surgeon may only partially inflate inflatable portion 330. The surgeon may then insert a surgical access portal "S2" through lumen 316 of housing 310 and further inflate inflatable portion 330 to reduce the diameter of lumen 316 such that lumen 316 presses against surgical access portal "S2" and forms a substantially fluid-tight seal therewith. In this way a surgical access portal of standard size may be utilized through an incision in tissue or naturally occurring orifice which has a larger diameter than the surgical access portal. Once the operation is complete the surgeon may fully or partially evacuate inflatable portion 330 to remove surgical access portal "S2" from housing 310 and housing 310 from the orifice or incision in tissue "T".

Figure 10:
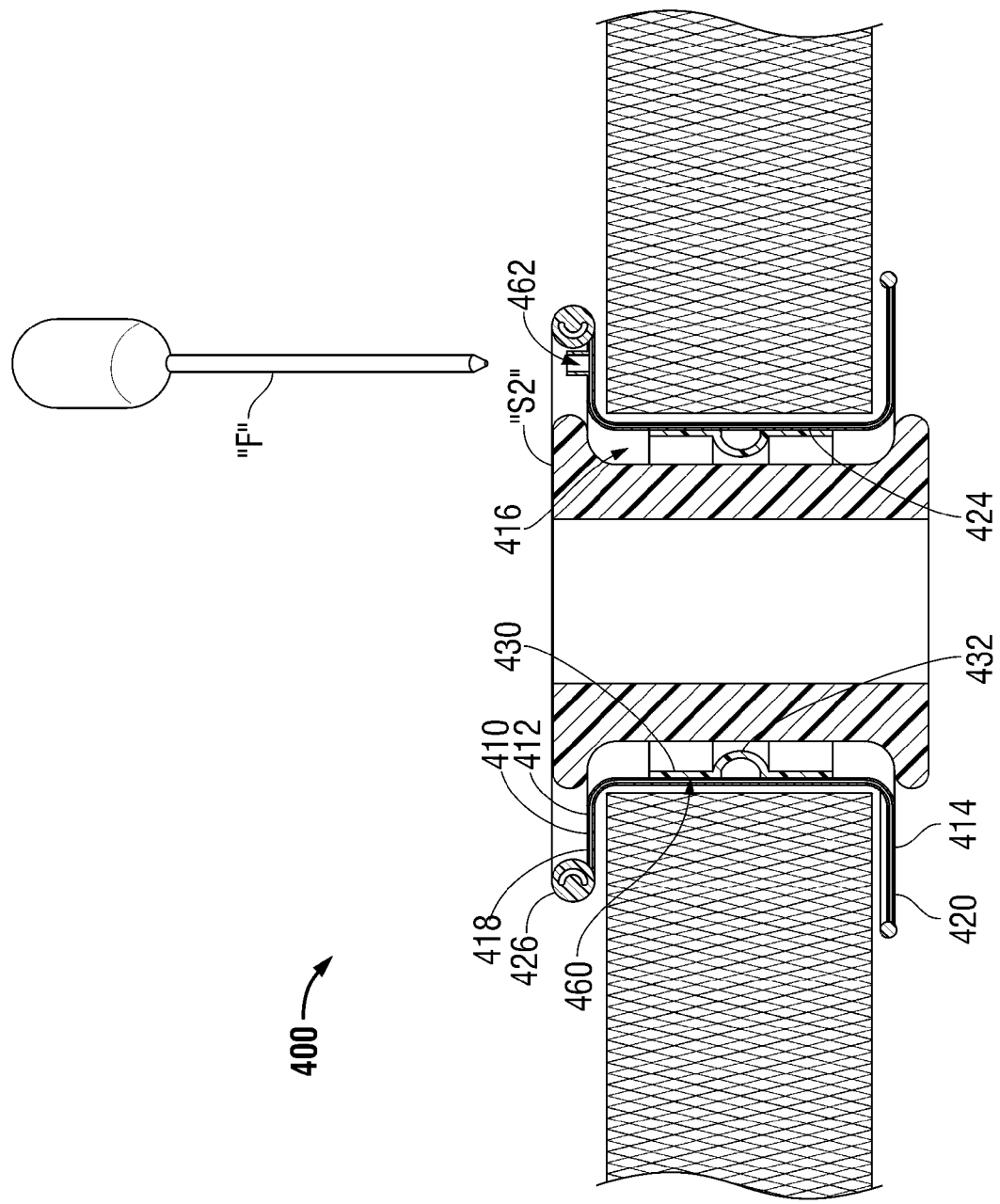
FIG. 10 is a side cut-away view of an alternate embodiment the surgical access device of FIG. 1 with the inflatable portion on the interior surface of the lumen.
Figure 11:
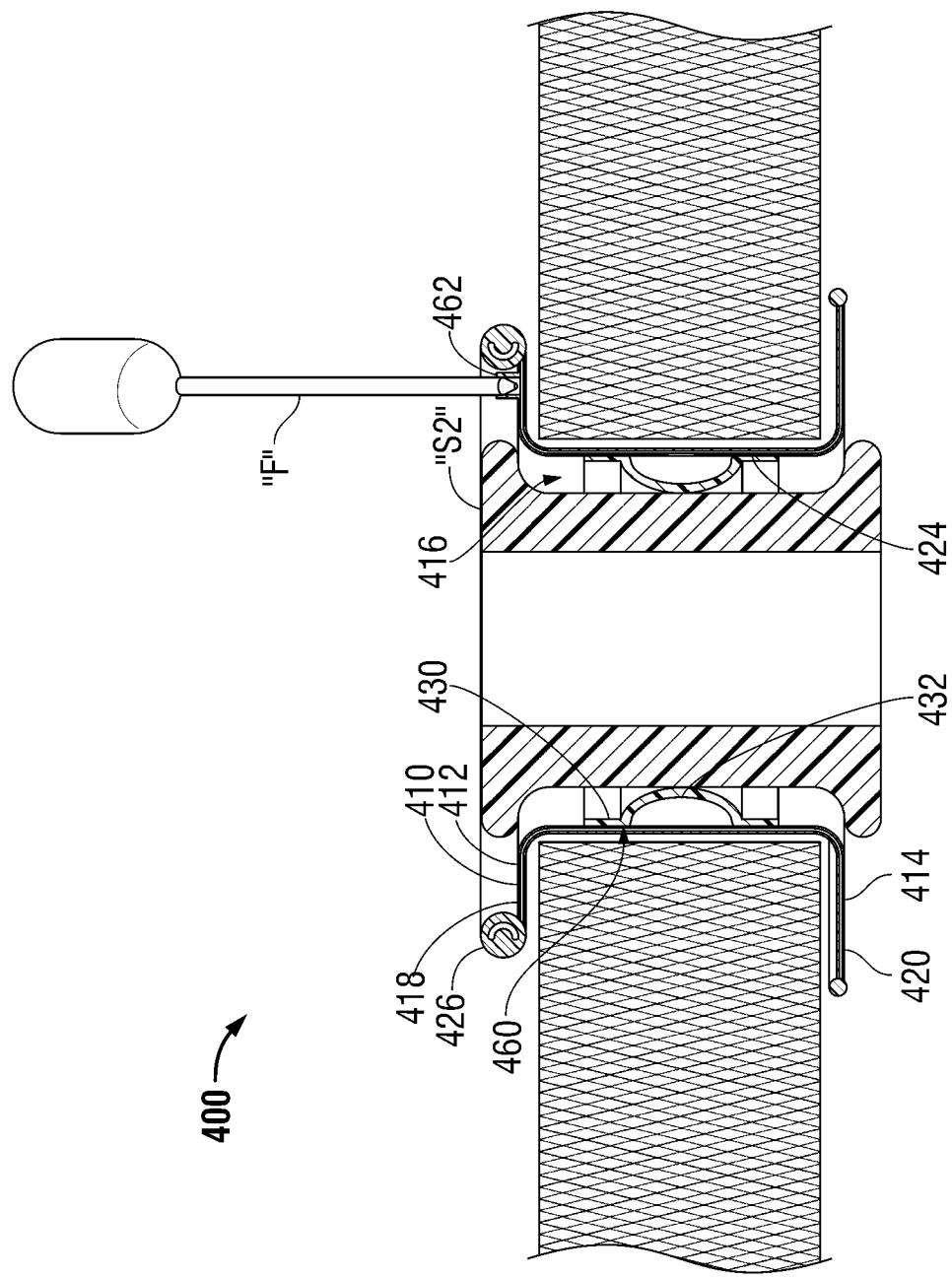
FIG. 11 is a side cut-away view of the surgical access device of FIG. 10 with the inflatable portion in the inflated state.

Referring now to FIGS. 10 and 11, in yet another embodiment which is similar to the previous embodiments, surgical access device 400 includes a housing 410 and an inflatable portion 430 disposed on housing 410. Housing 410 is insertable into an orifice or incision in tissue "T" and defines a "U" shaped cross-section including flanged portions 418 and 420 at proximal and distal ends 412 and 414 respectively. It is further contemplated that proximal end 412 may include an arcuate or crescent shaped ring 426 around which at least a portion of housing 410 is wrapped such that rotation of ring 426 allows the length of housing 410 to be extended or reduced at proximal end 412. Housing 410 also includes a lumen 416 extending therethrough for the reception of a surgical access port "S2" in a substantially fluid-tight manner. It is contemplated that lumen 416 may also receive other surgical objects as known in the art.

Inflatable portion 430 extends along interior surface 424 of lumen 416 between proximal end 412 and distal end 414 of housing 410. Inflatable portion 430 may extend the full length of interior surface 424 or may only extend over a portion of interior surface 424. Inflatable portion 430 includes a central portion 432 which is spaced from interior surface 424 and defines a substantially semi-circular cross-section. Central portion 432 reduces the diameter of lumen 416 upon inflation to accommodate surgical objects or surgical access portals "S2" of varying size. It is contemplated that when in the deflated state, central portion 432 may be proximate to or abutting interior surface 424. Housing 410 may include an inflation lumen 460 in fluid communication with inflatable portion 430 and defining an opening 462 for the reception of a fluid source "F". Inflation lumen 460 may be disposed within housing 410 or alternatively may be disposed on interior surface 424 or exterior surface 422 of housing 410.

During use, a surgeon inserts housing 410 into an incision in tissue "T" with inflatable portion 430 in the deflated state. The surgeon may adjust the length of housing 410 by rotating ring 426 clockwise or counter-clockwise depending on the depth of the incision in tissue "T". Once housing 410 is positioned properly the surgeon attaches a fluid source "F" to opening 462 and also inserts surgical access portal "S2" through lumen 416. The surgeon then provides fluid from fluid source "F" to inflatable portion 430 via inflation lumen 460 to transition inflatable portion 430 from the deflated state to the inflated state. This causes central portion 432 to separate from interior surface 424 and to press against surgical access portal "S2" and create a substantially fluid-tight seal therewith. Inflation of inflatable portion 430 also acts to force outer surface 422 of housing 410 against the incision in tissue "T" to form a substantially fluid-tight seal therewith. In this way a surgical access portal of standard size may be utilized through an incision in tissue or naturally occurring orifice which has a larger diameter than the surgical access portal. Once the operation is complete the surgeon may fully or partially evacuate inflatable portion 430 to remove surgical access portal "S2" from housing 410 and housing 410 from the orifice or incision in tissue "T".

Although the present disclosure has been described with respect to preferred embodiments, it will be readily apparent, to those having ordinary skill in the art that changes and modifications may be made thereto without departing from the spirit or scope of the subject device.

The invention claimed is:

1. A surgical access device, comprising:
a housing adapted for insertion into an incision in tissue, the housing defining a proximal end and a distal end and defining a lumen extending therethrough for the reception of a surgical access portal;
at least one inflatable portion disposed on the housing, the at least one inflatable portion having a deflated state and an inflated state, the housing adapted for insertion into an incision in tissue when the at least one inflatable portion is in the deflated state, the housing adapted to form a substantially fluid tight seal with an incision in tissue and with a surgical access portal inserted therethrough when the at least one inflatable portion is in the inflated state, the at least one inflatable portion including a lumen extending therethrough; and a slide member extending through the lumen of the inflatable portion and directly attached to an exterior surface of the housing, the position of the at least one inflatable portion being slidably adjustable along the slide member.

2. The surgical access device of claim 1, wherein the at least one inflatable portion further includes a partially inflated state.

3. The surgical access device of claim 1, wherein the at least one inflatable portion fully surrounds the housing.

4. The surgical access device of claim 1, wherein the at least one inflatable portion is disposed on an exterior surface of the housing.

5. The surgical access device of claim 4, wherein the at least one inflatable portion is slidable proximally and distally along the exterior surface of the housing.

6. The surgical access device of claim 1, wherein the at least one inflatable portion is disposed on an interior surface of the housing.

7. The surgical access device of claim 4, wherein the at least one inflatable portion is disposed on both the exterior surface and an interior surface of the housing.

8. The surgical access device of claim 1, wherein the at least one inflatable portion is three inflatable portions.

9. The surgical access device of claim 1, wherein the housing is a wound protector that may be selectively shortened by a user rolling a portion thereof.

10. The surgical access device of claim 1, wherein the slide member further includes a guide ring disposed at a proximal end, the guide ring adapted to guide a tube toward the at least one inflatable portion.

11. The surgical access device of claim 10, wherein the tube is adapted to actuate the at least one inflatable portion proximally and distally along the slide member.

12. The surgical access device of claim 1, wherein the at least one inflatable portion further includes a tube extending proximally therefrom, the tube adapted to provide fluid to the at least one inflatable portion from a fluid source connected thereto.

13. The surgical access device of claim 12, wherein the tube is disposed within the housing.

14. The surgical access device of claim 12, wherein the tube is disposed on the housing.

15. The surgical access device of claim 1, the housing further including a crescent shaped ring disposed at the proximal end, at least a portion of the housing being wrapped around the ring, the ring being rotatable to increase or decrease the length of the housing.

16. A method of providing surgical access through a large incision in tissue, the method comprising the steps of:
providing a surgical access portal, the surgical access portal including at least one lumen extending therethrough and adapted for sealed reception of a surgical object therethrough;
providing a surgical access device comprising:
a housing adapted for insertion into an incision in tissue, the housing defining a proximal end and a distal end and defining a lumen extending therethrough for the reception of the surgical access portal; and
at least one inflatable portion disposed on the housing, the at least one inflatable portion having a deflated state and an inflated state, the housing being insertable into the incision in tissue when the at least one inflatable portion is in the deflated state, the housing forming a substantially fluid tight seal with the incision in tissue and with a surgical access portal inserted therethrough when the at least one inflatable portion is in the inflated state;
inserting the housing into the incision in tissue;
at least partially inflating the at least one inflatable portion to secure the housing within the incision in tissue;
inserting the surgical access portal through the lumen of the housing; and
further inflating the at least one inflatable portion to secure the surgical access portal within the lumen.

17. The method of claim 16, wherein the at least one inflatable portion is slideable proximally and distally along an exterior surface of the housing and further including the step of sliding the at least one inflatable portion proximally or distally along the exterior surface of the housing.

18. The method of claim 16, wherein the surgical access device further includes a tube extending proximally from the housing and in fluid communication with the at least one inflatable member, the method further including the steps of attaching a fluid source to the tube and dispensing fluid to the at least one inflatable portion.

* * * * *